United States Patent [19]
Maaz

[11] Patent Number: 4,840,614
[45] Date of Patent: Jun. 20, 1989

[54] GASTRIC TUBE POSITIONING METHOD

[76] Inventor: Bassam Maaz, 637 Avant La., N., Memphis, Tenn. 38105

[21] Appl. No.: 140,612

[22] Filed: Jan. 4, 1988

[51] Int. Cl.⁴ .............................. A61M 31/00
[52] U.S. Cl. .............................. 604/53; 604/54
[58] Field of Search .............................. 604/28, 36, 37, 48, 604/49, 54, 31, 247, 319, 321, 323, 53

[56] References Cited

U.S. PATENT DOCUMENTS 3,463,159 8/1969 Heimlich .............................. 604/247
3,982,540 9/1976 Ross .............................. 604/54

*Primary Examiner*—C. Fred Rosenbaum
*Assistant Examiner*—J. L. Kruter
*Attorney, Agent, or Firm*—Leon Gilden

[57] ABSTRACT

A gastric tube positioning method includes an improved check valve operative in cooperation with a gastric tube positionable within a patient. Should mis-alignment of the tube occur, including introduction of the tube into the lung region of a patient, the other distal end of the tube positioned within a container of fluid will emit a plurality of bubbles indicating lung positioning of the tube wherein the improved check valve assembly prevents said fluid from introduction into the lung cavity.

1 Claim, 1 Drawing Sheet

Fig 1
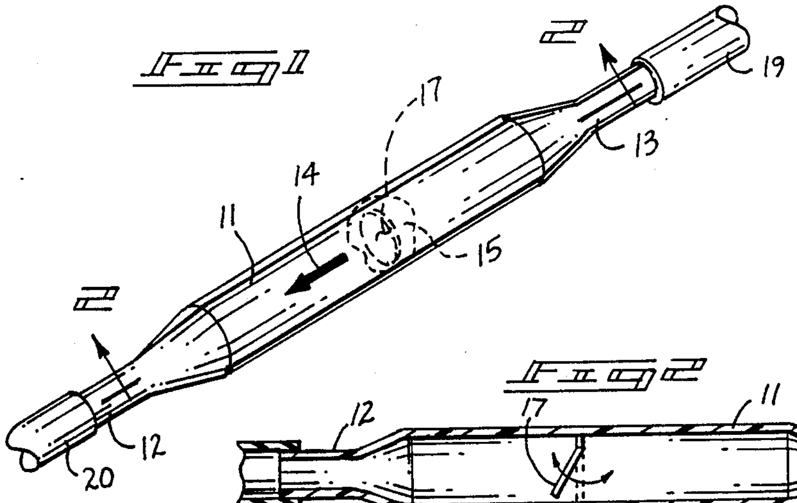
Fig 2
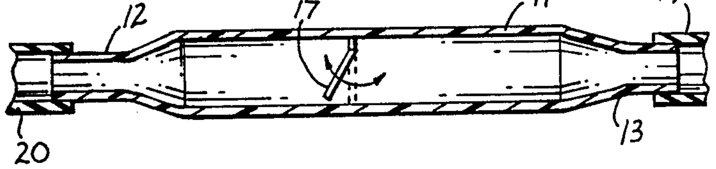
Fig 3
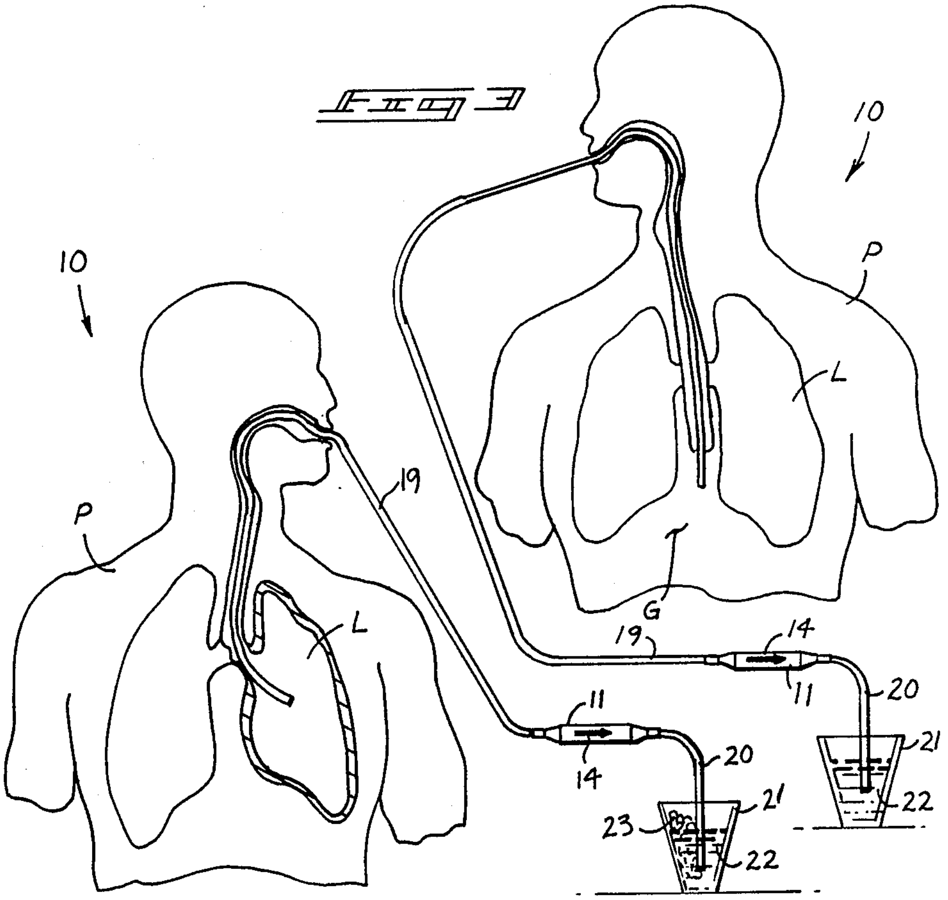
Fig 4

GASTRIC TUBE POSITIONING METHOD

BACKGROUND OF THE INVENTION

1. Field of the Invention

The present invention relates to the utilization of gastric tubes and their use by patients requiring nourishment through the use of such tubes. Occasionally the tube is mispositioned in use and is introduced into a lung region with attendant deleterious results should introduction of nourishment be attempted. The use of x-rays and the like are not satisfactory in the confirmation of appropriate positioning of such tubes internally of individuals due to the attendant risk of x-ray overexposure. Additionally, this class of tube is frequently of a composition that does not present or enable x-ray verification of appropriate positioning and accordingly error in the placement of such a tube, as noted above, may not be discovered until misuse of the tube has occurred.

In this respect, the instant invention attempts to overcome deficiencies of the prior art by utilizing an improved check valve unit positioned in registration with the gastric tube and upon positioning of the tube within a patient, the other end of the tube remote from the check valve assembly is positioned within a container of fluid whereupon indication of bubbling in the fluid graphically denotes the mispositioning of the tube in the patient. The improved valve assembly in this method prevents introduction of fluid into a lung cavity should the tube be mispositioned in such cavity.

2. Description of the Prior Art

The use of check valves is well known in the prior art. As may be appreciated, these devices are utilized wherever one-way directional flow of a fluid is desired. In this connection, there are several examples of check valve assemblies that are utilized in various environments. For example, U.S. Des. Pat. No. 202,701 to Davis, U.S. Des. Pat. No. 232,635 to Mauri, U.S. Des. Pat. No. 239,021 to D'Alo, U.S. Des. Pat. No. 245,921 to Beran, and U.S. Des. Pat. No. 269,633 to Willinger are patents representative of devices that are utilized as check valves in a variety of environments.

As such, however, it may be appreciated that there is a continuing need for a new and improved method for determining the proper positioning of a gastric tube within a patient which addresses both the problem of convenience and effectiveness, and in this respect the present invention substantially fulfills this need.

SUMMARY OF THE INVENTION

In view of the foregoing disadvantages inherent in the known types of gastric tube positioning methods now present in the prior art, the present invention provides a gastric tube positioning method wherein a gastric tube including an improved check valve assembly when presented within a patient at one end is initially positioned within a container of fluid at the other end for determining the appropriate positioning of the tube within the patient. As such, the general purpose of the present invention, which will be described subsequently in greater detail, is to provide a new and improved gastric tube positioning method which has all the advantages of the prior art gastric tube positioning methods and none of the disadvantages.

To attain this, the present invention comprises an elongate gastric tube of conventional construction including a check valve assembly wherein a flapper closure is normally biased in a closed position and is pivotal to an open position by normal pressure occurring in the respiratory process. Accordingly, a bubbling effect will occur within the fluid-filled container to indicate malpositioning of the aforenoted gastric tube. The valve assembly accordingly prevents introduction of fluid within a lung cavity by means of the normally biased flapper valve that upon inhalation remains in a closed position. Conversely, appropriate positioning of the gastric tube assembly will produce no bubbling effect within the fluid filled container.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is of enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved gastric tube positioning method which has all the advantages of the prior art gastric tube positioning methods and none of the disadvantages.

It is another object of the present invention to provide a new and improved gastric tube positioning method which may be easily and effeciently manufactured and marketed.

It is a further object of the present invention to provide a new and improved gastric tube positioning method which is of a durable and reliable construction.

An even further object of the present invention is to provide a new and improved gastric tube positioning method which is susceptible of a low cost of manufacture with regard to both materials and labor, and which accordingly is then susceptible of low prices of sale to the consuming public, thereby making such gastric tube positioning method economically available to the buying public.

Still yet another object of the present invention is to provide a new and improved gastric tube positioning method which provides in the apparatuses and methods of the prior art some of the advantages thereof, while simultaneously overcoming some of the disadvantages normally associated therewith.

Still another object of the present invention is to provide a new and improved gastric tube positioning method wherein an improved check valve assembly is positioned in line with an associated gastric tube that upon positioning of one end of said gastric tube within a patient and the other end within a fluid-filled container, malpositioning of the gastric tube within the patient as in a lung cavity will produce the effect of bubbling within the fluid container and accordingly prevent introduction of fluid within the lung cavity.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the improved check valve as utilized in the instant invention.

FIG. 2 is an orthographic side view of the instant invention of FIG. 1 taken along the lines 2—2 in the direction indicated by the arrows.

FIG. 3 is an isometric diagrammatic representation of the gastric tube introduced and appropriately positioned within a patient.

FIG. 4 is an orthographic diagrammatic representation of the gastric tube assembly mispositioned within a patient.

DESCRIPTION OF THE PREFERRED EMBODIMENT

With reference now to the drawings, and in particular to FIGS. 1, 2, 3 and 4 thereof, a new and improved gastric tube positioning method embodying the principles and concepts of the present invention and generally designated by the reference numeral 10 will be described.

More specifically, it will be noted that the gastric tube positioning method includes a check valve assembly 11 formed with a tapering forward tube receiving portion 12 and a tapering rear tube receiving portion 13. Indication arrow 14 oriented on the check valve body 11 indicates the direction of fluid flow available in use of the check valve.

Attention to FIG. 2 illustrates a perimeter opening frame portion 15 defining an opening 17 positioned somewhat medially of the check valve 11. A flexible planar membrane closure element 16 is pivotally biased to a normally closed orientation, as indicated in phantom in FIG. 2, and is pivotally movable per the arrow indication 18. The membrane portion 16 is of a memory retentent material normally biased in the closed position, as illustrated in phantom.

Attention to FIGS. 3 and 4 illustrate the use of the valve 11 in cooperation with a rearwardly direction gastric tube 19 secured to rear portion 13 of the check valve with a forward gastric tube 20 secured to forward portion 12 of the check valve 11. FIG. 3 indicates a correct positioning of a gastric tube within a patient "P" and is directed into the gastric portion of a patient and accordingly normal respiration of the patient "P" produces no effect when forward tube 20 is positioned within a container 21 containing a level of fluid 22. Conversely, when a gastric tube portion 19 is mispositioned, as in FIG. 4, into a lung region, with the check valve 11 appropriately directed per arrow 14 is a quantity of bubbles or foaming 23 will occur within fluid 22 during a normal exhalation of patient "P". The check valve 11 in its normal operation prevents intake of fluid by the patient "P" as the membrane will maintain its closed position upon inhalation by a patient with the membrane tension being such that normal exhalation will unseat the membrane from perimeter frame portion 15 only during exhalation.

The manner of usage and operation of the present invention should be apparent from the above description. Accordingly, no further discussion relative to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A method for proper positioning of a gastric feed tube within a patient comprising, securing a first gastric tube portion onto a forward end of a valve means, and securing a second gastric tube portion onto a rearward end of said valve means, and directing said second gastric tube portion through a patient's esophagus, and temporarily positioning a terminal end portion of said first gastric tube portion within a liquid and observing the liquid for presence of bubbling emanating from said terminal end within said liquid to ascertain the positioning of the second gastric tube portion either within a patient's stomach wherein no bubbling occurs, or within the patient's gastric tube portion by the presence of bubbling within said liquid, and further forming said valve means with an internal flexible membrane normally seated over a defined opening within said valve means enabling fluid flow from said rearward end of said valve means to a said forward end of said valve means only, and forming said flexible membrane of a memory retentent material and of a force to normally seat said membrane against a frame portion defining said opening wherein said normal forces of seating is less than that of exhalation pressure of an individual during a normal respiratory process.

* * * * *